(12) United States Patent
May et al.

(10) Patent No.: US 7,285,553 B2
(45) Date of Patent: Oct. 23, 2007

(54) SEROTONERGIC 5HT₇ RECEPTOR COMPOUNDS FOR TREATING OCULAR AND CNS DISORDERS

(75) Inventors: Jesse A. May, Fort Worth, TX (US); Thomas R. Dean, Weatherford, TX (US); Najam A. Sharif, Arlington, TX (US); Hwang-Hsing Chen, Fort Worth, TX (US)

(73) Assignee: Alcon Manufacturing, Ltd., Fort Worth, TX (US)

( * ) Notice: Subject to any disclaimer, the term of this patent is extended or adjusted under 35 U.S.C. 154(b) by 0 days.

(21) Appl. No.: 11/265,030

(22) Filed: Nov. 2, 2005

(65) Prior Publication Data

US 2006/0052372 A1 Mar. 9, 2006

Related U.S. Application Data

(62) Division of application No. 11/100,918, filed on Apr. 7, 2005, now Pat. No. 7,060,704, which is a division of application No. 09/674,403, filed as application No. PCT/US99/10179 on May 10, 1999, now Pat. No. 6,960,579.

(60) Provisional application No. 60/086,006, filed on May 19, 1998, provisional application No. 60/086,005, filed on May 19, 1998, provisional application No. 60/086,002, filed on May 19, 1998, provisional application No. 60/085,989, filed on May 19, 1998.

(51) Int. Cl.
  *C07D 403/00* (2006.01)
  *C07D 401/00* (2006.01)
  *C07D 241/04* (2006.01)
  *A61K 31/495* (2006.01)

(52) U.S. Cl. .................. 514/255.03; 544/359; 544/360; 544/383; 544/392; 544/398

(58) Field of Classification Search ................ 544/392, 544/160, 359, 360, 383, 398; 546/246; 514/255.03
See application file for complete search history.

(56) References Cited

U.S. PATENT DOCUMENTS

| | | | |
|---|---|---|---|
| 3,303,189 A | 2/1967 | Loev | 260/243 |
| 4,330,542 A * | 5/1982 | Descamps et al. | 514/238.2 |
| 5,011,846 A | 4/1991 | Gittos et al. | 514/294 |
| 5,106,855 A | 4/1992 | McLees | 514/317 |
| 5,130,313 A * | 7/1992 | Comte et al. | 514/253.03 |
| 5,153,192 A | 10/1992 | Dean et al. | 514/226.5 |
| 5,290,781 A | 3/1994 | Espino et al. | 514/259 |
| 5,344,929 A | 9/1994 | Dean et al. | 544/48 |
| 5,470,973 A | 11/1995 | Hoff | 544/48 |
| 5,494,928 A | 2/1996 | Bös | 514/415 |
| 5,538,966 A | 7/1996 | May et al. | 54/226.5 |
| 5,538,974 A | 7/1996 | Ogawa et al. | 514/253 |
| 5,561,150 A | 10/1996 | Wichmann | 514/406 |
| 5,646,173 A | 7/1997 | Bös et al. | 514/411 |
| 5,652,272 A | 7/1997 | Ogawa et al. | 514/652 |
| 5,693,654 A | 12/1997 | Birch | 514/323 |
| 5,773,437 A | 6/1998 | Masaki et al. | 514/224.2 |
| 5,874,429 A | 2/1999 | Mizuno et al. | 514/226.5 |
| 5,880,134 A | 3/1999 | Cohen et al. | 514/288 |
| 5,902,815 A | 5/1999 | Olney et al. | 514/285 |
| 6,107,324 A | 8/2000 | Behan et al. | 514/406 |
| 6,271,223 B1 | 8/2001 | Mizuno et al. | 514/211.1 |
| 6,660,870 B1 | 12/2003 | Ruskinko et al. | 548/307.4 |
| 6,664,286 B1 | 12/2003 | May et al. | 514/415 |
| 6,696,476 B2 | 2/2004 | Chen et al. | 514/403 |
| 6,806,285 B1 | 10/2004 | May et al. | 514/416 |
| 6,884,816 B2 | 4/2005 | May et al. | 514/405 |
| 2003/0181503 A1 | 9/2003 | May et al. | 514/406 |

FOREIGN PATENT DOCUMENTS

| | | |
|---|---|---|
| EP | 0522226 A1 | 1/1993 |
| EP | 0738513 A1 | 10/1996 |
| EP | 0771563 A2 | 5/1997 |
| JP | 37010770 | 8/1962 |
| WO | WO92/19606 * | 11/1992 |
| WO | WO92/20338 | 11/1992 |
| WO | WO94/03162 | 2/1994 |
| WO | WO95/19981 | 7/1995 |
| WO | WO97/17345 | 5/1997 |
| WO | WO97/29097 | 8/1997 |
| WO | WO97/48681 | 12/1997 |

(Continued)

OTHER PUBLICATIONS

Nesmeyanov et al. (Doklady Akademii Nauk SSSR (1961), 136, 836-9). Abstract.*

Goldenberg et al. European Journal of Medicinal Chemistry (1980), 15(6), 545-50. Abstract.*

Ahmad, "Fluoxetine and glaucoma,"*Annals of Pharmacother.*, vol. 25:436, (1992).

Barnet and Osborne, "The Presence of Serotonin (5-HT₁) Receptors Negatively Coupled to Adenylate Cyclase in Rabbit and Human Iris-Ciliary Processes," *Exp. Eye Res.*, vol. 57:209-216 (1993).

Chang et al., "Mechanism of the Ocular Hypotensive Action of Ketanserin," *J. Ocular Pharmacol*, vol. 1(2):137-147 (1985).

Chidlow et al., "Characteristics of [³H]5-Hydroxytryptamine Binding to Iris—Cilary Body Tissue of the Rabbit," *Invest. Ophthalmol. Vis. Sci.*, 36(11):2238-2245 (1995).

(Continued)

*Primary Examiner*—Bruck Kifle
(74) *Attorney, Agent, or Firm*—Patrick M. Ryan

(57) ABSTRACT

Compounds with 5HT₇ receptor affinity (some of which are novel) useful for lowering IOP, improving blood flow to the optic nerve head and the retina, providing neuroprotection, and treating retinal diseases are disclosed. The Compounds are also useful for treating sleep disorders, depression, and other psychiatric disorders, such as, schizophrenia, anxiety, obsessive compulsive disorder, circadian rhythm disorders, and centrally and peripherally mediated hypertension. Compositions and methods for their use are also disclosed.

2 Claims, No Drawings

FOREIGN PATENT DOCUMENTS

| | | |
|---|---|---|
| WO | WO97/49695 | 12/1997 |
| WO | WO98/00400 | 1/1998 |
| WO | WO98/18458 | 5/1998 |
| WO | WO99/59499 | 11/1999 |
| WO | WO 00/12475 | 3/2000 |
| WO | WO 00/12510 | 3/2000 |
| WO | WO 00/35922 | 6/2000 |
| WO | WO 00/44753 | 8/2000 |
| WO | WO 01/40183 | 6/2001 |
| WO | WO 01/70207 | 9/2001 |
| WO | WO 01/70223 | 9/2001 |
| WO | WO 01/70230 | 9/2001 |
| WO | WO 01/70701 | 9/2001 |
| WO | WO 01/70702 | 9/2001 |
| WO | WO 01/70745 | 9/2001 |
| WO | WO 02/098350 | 12/2002 |
| WO | WO 02/098400 | 12/2002 |
| WO | WO 02/098860 | 12/2002 |
| WO | WO 03/051291 | 6/2003 |
| WO | WO 03/051352 | 6/2003 |
| WO | WO 03/053436 | 7/2003 |
| WO | WO 2004/019874 | 3/2004 |
| WO | WO 2004/028451 | 4/2004 |
| WO | WO 2004/054572 | 7/2004 |
| WO | WO 2004/058725 | 7/2004 |

OTHER PUBLICATIONS

Chiou et al., "Effects of Antiglaucoma Drugs on Ocular Blood Flow in Ocular Hypertension Rabbits," *J. Ocular Pharmacol*, vol. 9(1):13-24 (1993).

Costagliola et al., "Effect of Oral Ketanserin Administration on Intraocular Pressure in Glaucomatous Patients," *Ex. Eye Res.*, vol. 52:507-510 (1991).

Costagliola et al., "Fluoxetine Oral Administration Increases Intraocular Pressure," *Br. J. Ophthalmol.*, vol. 80:678 (1996).

Eglen et al., "The 5-$HT_7$ Receptor: Orphan Found," *Trend Pharmacol. Sci.*, vol. 18:104-107 (1997).

Gupta et al., "Therapeutic Potentials of 5-HT Receptor Modulators," Indian J. of Pharmacology, vol. 26, pp. 94-107 (1994).

Heidmann et al, Four-5-Hydroxytryptamine$_7$ (5-$HT_7$) Receptor Isoforms in Human and Rat Produced by Alternative Splicing: Species Differences Due to Altered Intron-Exon Organization, *J. Neurochem*, vol. 68(4): 1372-1381 (1997).

Hoyer et al., "VII. International Union of Pharmacology Classification of Receptors for 5-Hydroxytryptamine (Serotonin)," *Pharmacol Rev.*, vol. 46(2):157-203 (1994).

Jae et al., "Pyrrolidine-3-carboxylic Acids as Endothelin Antagonists. 2. Sulfonamide Based $_{ETA/ETB}$ Mixed Antagonists," *J. Med. Chem.*, vol. 40:3217-3227 (1997).

Krootila et al., "Effect of Serotonin and Its Antagonist (Ketanserin) on Intraocular Pressue in the Rabbit," *J. Ocular Pharmacol.*, vol. 3(4):279-290 (1987).

Mallorga et al., "characterizationof serotonin receptors in the iris + ciliary body of the albino rabbit," *Curr. Eye Res.* , vol. 6(3):527-532 (1987).

Mano et al. "The Effect of Anplag (Sarpogrelate HCl), New Selective 5-$HT_2$ Antagonist on Intraocular Pressure in Rabbits," *Invest. Opthal. Vis. Sci.*, vol. 36(Suppl):3322- (1995).

Martin et al., "Serotonin in Human Aqueous Humor," *Ophthalmol.*, vol. 95(9):1221-1226 (1988).

Martin et al., "The structure and signalling properties of 5-HT receptors: an endless diversity?", *Trends in Pharamacological Science*, vol. 19, pp. 2-4 (1998).

May et al., "A Novel and Selective 5-$HT_2$ Receptor Agonist with Ocular Hypotensive Activity: (S)-(+)-1-(2-Aminopropyl)-8,9-dihydropyrano[3,2-e]indole," *J. Med. Chem.*, vol. 46, pp. 4188-4195 (2003).

May et al., "Evaluation of the Ocular Hypotension Response of Serotonin 5-$HT_{1A}$ and 5-$HT_2$ Receptor Ligands in Conscious Ocular Hypertensive Cynomolgus Monkeys," *J. of Pharmacology and Experimental Therapeutics*, vol. 306(1), pp. 301-309 (2003).

Meyer et al., Topical Application of Serotonin or the 5-$HT_1$-Agonist 5-CT Intraocular Pressure in Rabbits, *Invest. Ophthalmol. Vis. Sci.*, vol. 34(1):3035-3042 (1993).

Osborne et al., "Do-Beta Adrenoceptors and Serotonin 5-$HT_{1A}$ Receptors Have Similar Functions in the Control of Intraocular Pressure in the Rabbit?", *Ophthalmologica*, vol. 210-308-314 (1996).

Osborne et al., "5-Hydroxytryptamine$_{1A}$ agoists: potential use in glaucoma. Evicence from animal studies," *Eye*, vol. 14(38), pp. 454-463 (2000).

Sianesi et al., "New Benzothiazines. 4.[1] 1H-2,3-Benzothiazin-4(3H)-one,2,2-Dioxide and 2H-1,2-Benzothiazin-3(4H)-one 1,1-Dioxide Nitrogen Derivatives with Central Nervous System Activity," *J. of Medicinal Chemistry*, vol. 16(10), pp. 1133-1137 (1973).

Takenaka et al., "The Effect of Anplag (Sarporelate HCL), Novel Selective 5-$HT_2$ Antagonist on Intraocular Pressure in Glaucoma Patients," *Invest Ophthal. Vis. SCi.*, vol. 36 (Suppl):3390-377, (1995).

Tobin et al., "Evidence for the Presence of Serotonergic Nerves and Receptors in the Iris-Ciliary Body J. Complex of Rabbit," *J. of Neurosci.*, vol. 8(10):3713-3721 (1988).

Tobin et al., "Evidence for the Presence of Serotonin Receptors Negatively Coupled to Adenylate Cyclase in the Rabbit Iris-Ciliary Body," *J. Neurochem.*, vol. 53(3):686-601, 1989.

Wang et al., "Effect of 5-methylurapidil, an $\alpha_{1a}$-adrenergic antagonist and 5-hydroxytryptamine$_{1a}$ agonist, on aqueous humor dynamics in monkeys and rabbits," *Curr. Eye Res.*, vol. 16:769-775 (1997).

Wang et al., Effect of $_p$-MPPI Hydrochloride ($_p$-MPPI) Applid Before 5-methylurapidil (5-MU) on Intraocular Pressure, *Invest. Ophthal. Vis. Sci.*, vol. 39 (Suppl):2236-2488 (1988).

Zifa et al., "5-Hydroxytryptamine Receptors," *Pharmacol. Rev.*, vol. 44(3):401-458 (1992).

Zinnes et al., "1,2-Benzothiazines. III. The Preparation of 2H-1,2-Benzothiazin-4(3H)-one 1,1-Dioxide by the Acid-Catalyzed Deacetylation of β-Diketone," *J. Org. Chem.*, vol. 31:162-165 (1966).

Hayashi et al., "Analgesics. I. Pharmacological effects of acyl derivatives of aminoalkylaniline," *Yakugaku Zasshi*, vol. 83, pp. 62-73 (1963) (abstract only).

Nesmeyanov et al., "Indole ring closure of azobenzene with cyclohexanone," *Doklady Akademii Nauk SSSR*, vol. 136, p. 836-839 (1961) (untranslated; independent English abstract provided).

Shigematsu, "Synthetic analgesics, XIV. Synthesis of ethyl N-(t-tertiary aminoalkyl)carbaanilates and N-(2-tertiary aminoalkyl) ethanesulfamilides," *Yakugaku Zasshi*, vol. 81, pp. 423-426 (1961).

\* cited by examiner

SEROTONERGIC 5HT₇ RECEPTOR COMPOUNDS FOR TREATING OCULAR AND CNS DISORDERS

This application is a divisional application of U.S. Ser. No. 11/100,918, filed Apr. 7, 2005, now U.S. Pat. No. 7,060,704, which is a divisional application of U.S. Ser. No. 09/674,403, filed Oct. 31, 2000, now U.S. Pat. No. 6,960,579, which is a 371 application of PCT/US99/10179, filed May 10, 1999, which claims priority from U.S. Provisional Applications, U.S. Ser. No. 60/086,006, filed May 19, 1998, U.S. Ser. No. 60/086,005, filed May 19, 1998, U.S. Ser. No. 60/086,002, filed May 19, 1998, and U.S. Ser. No. 60/085,989, filed May 19, 1998.

The present invention is directed to the use of compounds with serotonergic $5HT_7$ receptor affinity (Compound) (some of which are novel), to improve blood flow to the optic nerve head and the retina, provide neuroprotection, lower intraocular pressure (IOP), and treat retinal diseases, such as, glaucoma, age related macular degeneration (ARMD), optic neuritis, ischemic disorders, diabetic retinopathy, and retinal edema. The Compounds are also useful for treating sleep disorders, depression, and other psychiatric disorders, such as, schizophrenia, anxiety, obsessive compulsive disorder, circadian rhythm disorders, and centrally and peripherally mediated hypertension.

BACKGROUND OF THE INVENTION

Serotonin (5-hydroxy tryptamine; 5HT) is an endogenous biogenic amine with a well defined neurotransmitter function in many tissues of the body including the eye [Zifa and Fillion, *Pharmacol. Rev.*, 44:401-458, 1992; Hoyer et al., *Pharmacol. Rev.*, 46:157-203, 1994; Tobin et al., *J. Neurosci.*, 8:3713-3721, 1988].

5HT can interact with at least seven major 5HT receptors ($5HT_1$-$5HT_7$) and additional subtypes within these families to initiate intracellular biochemical events such as stimulation of second messengers (e.g. cAMP, inositol trisphosphate) eventually leading to the final biological response, for example, tissue contraction or hormone release, etc. [Hoyer et al., supra; Martin et al., *Trends Pharmacol. Sci.*, 19:2-4, 1998]. Receptor subtypes within the $5HT_1$ family are negatively coupled to adenylyl cyclase (AC) and cause inhibition of cAMP production, while $5HT_4$, $5HT_6$, and $5HT_7$ receptors are positively coupled to AC and thus stimulate cAMP production when activated by 5HT [Martin et al., supra]. The receptors in the $5HT_2$ family are positively coupled to phospholipase C (PLC) and thus generate inositol phosphates and mobilize intracellular calcium when activated to mediate the effects of 5HT. The $5HT_3$ receptor is unique in that it couples to an ion channel which gates sodium, potassium, and calcium [Hoyer et al., supra].

The human and animal $5HT_7$ receptor has only recently been cloned, expressed, and shown to be present in various brain areas and peripheral tissues [Eglen et al., *Trend Pharmacol. Sci.*, 18:104-107, 1997]. Recent studies have shown there to be four splice variants of the $5HT_7$ receptor [Heidmann et al., *J. Neurochem.*, 68:1372-1381, 1997]. It has been proposed that the $5HT_7$ receptor may be involved in the pathophysiology of sleep disorders, depression, and other psychiatric disorders [Eglen et al., supra]. In the periphery, stimulation of $5HT_7$ receptors results in relaxation of blood vessels and hence vasodilation [Eglen et al., supra]. Improving blood flow to the back of the eye, including the retina, the macula, and the optic nerve head is believed to be beneficial in the treatment of a number of retinal diseases, for example, glaucoma, ARMD, and diabetic retinopathy [Chiou, et al., *J. Ocular Pharmacol.* 9:13-24 (1993)].

Serotonergic nerves innervate the eye [Tobin et al., *J. Neurosci.*, 8:3713-3721, 1988] and 5HT has been found in the aqueous humor of human eyes [Martin et al., *Ophthalmol.*, 95:1221-1226, 1988]. In addition, receptor binding sites for [³H]5HT have been demonstrated and pharmacologically characterized in the iris-ciliary body (ICB) of rabbits [Mallorga and Sugrue, *Curr. Eye Res.*, 6:527-532, 1987 and Chidlow et al., *Invest. Ophthalmol. Vis. Sci.*, 36:2238-2245, 1995]. These 5HT binding sites have been shown to be functionally coupled to second messenger generation in rabbits [Tobin and Osborne, *J. Neurochem.*, 53:686-601, 1989 and Tobin et al., *J. Neurosci*, supra]. In the human ICB these binding sites are characterized as $5HT_{1A}$ and $5HT_2$ receptors [Barnet and Osborne, *Exp. Eye Res.*, 57:209-216, 1993]. In addition, the presence of mRNAs for $5HT_{1a}$ and $5HT_7$ receptors in the rabbit ICB have been reported [Chidlow et al., *Invest. Ophthalmol. Vis. Sci.*, supra and Osborne and Chidlow, *Ophthalmologica*, 210:308-314, 1996]. The precise functions of these receptors in the eye are unknown, especially the $5HT_7$ subtype(s).

5HT or 5-carboxamidotryptamine (5-CT) topically applied to the rabbit eye raise intraocular pressure in the anterior chamber of the eye [Meyer-Bothling et al., *Invest. Ophthalmol. Vis. Sci.*, 34:3035-3042, 1993]. By contrast, it has been shown that topically applied 5HT lowers IOP [Krootila et al., *J. Ocular Pharmacol.*, 3:279-290, 1987 (intracamerally 5HT raised IOP and caused breakdown of the blood-aqueous barrier)]. In addition, the 5HT uptake inhibitor, fluoxetine (Prozac®), also raises IOP in human subjects upon oral administration [Costagliola et al., *Br. J. Ophthalmol.*, 80:678, 1996] and may cause glaucoma [Ahmad, *Ann. Pharmacother.*, 25:436, 1992]. However, the 5HT receptor subtype(s) involved in the IOP-elevating effects of 5HT, 5-CT and fluoxetine are unknown.

Studies conducted in rabbits with 8-hydroxy DPAT and MKC-242 ($5HT_{1A}$ agonists) have shown these compounds lower IOP [Osborne and Chidlow, *Ophthalmologica*, 210:308-319, 1996, and EP 0771563-A2]. In addition, 5-methylurapidil ($5HT_{1A}$ agonist) lowered IOP in glaucomatous monkeys [Wang, et al., *Curr. Eye Res.*, 16:679-775, 1997]. Both MKC-242 and 5-methylurapidil are relatively potent α1 receptor antagonists (α1 antagonists are known to lower IOP in rabbits, monkeys, and man). The mechanism of action for lowering IOP by 5-methylurapidil has been attributed to its α1 antagonist activity and not its $5HT_{1A}$ agonist activity [Wang, et al., *Invest. Ophthal. Vis. Sci.*, 39(Suppl): 2236-488, 1998]. U.S. Pat. No. 5,693,654, discloses $5HT_1$ receptor agonists for lowering IOP. WO92/20333 discloses certain $5HT_{1A}$ agonists for the treatment of glaucoma.

Methysergide ($5HT_2$ antagonist) lowered IOP in rabbits [Krootila, et al., *Esp. Eye Res.*, supra]. Ketanserin ($5HT_{2A/C}$ antagonist), also with significant α1 antagonist activity, lowers IOP in rabbits and man [Chan, et al., *J. Ocular Pharmacol.*, 1:137-147, 1985 and Costagliola, et al., *Ex. Eye Res.*, 52:507-510, 1991]. Saprogrelate ($5HT_{2A}$ antagonist) lowers IOP in rabbits and in man when dosed topically or orally [Mano, et al., *Invest. Ophthal. Vis. Sci.*, 36(Suppl): 3322-309, 1995, and Takenaka, et al., *Invest Ophthal. Vis. Sci.*, 36(Suppl):3390-377, 1995]. EP 522226 and U.S. Pat. No. 5,290,781 disclose the use of ketanserin and its derivatives for treating ocular hypertension. U.S. Pat. Nos. 5,290, 781 and 5,106,555 discloses the use of certain 5HT$_2$ antagonists for lowering IOP. U.S. Pat. No. 5,652,272 discloses saprogrelate for reducing IOP. U.S. Pat. No. 5,538,974 discloses opthalmic compositions of certain 5HT$_2$ antagonists for lowering IOP.

U.S. Pat. No. 5,011,846 discloses certain 5HT$_3$ receptor antagonists for treating glaucoma.

WO 97/17345 discloses that particular compounds with 5HT$_4$ serotonergic receptor agonist or antagonist activity are useful for treating psychiatric, gastrointestinal, lower urinary, and cardiovascular disorders. The publication mentions the compounds may also be useful for glaucoma.

As evidenced by the previous discussion, it is not clear which serotonergic receptor activity is responsible for lowering IOP. Moreover, a number of these compounds are known to have activity at other receptors which are known to be involved in lowering IOP. Furthermore, it has not been cleared which receptor(s) might be responsible for increasing blood flow and providing neuroprotection in the eye.

SUMMARY OF THE INVENTION

The present invention is directed to Compounds, some of which are novel, that have 5HT$_7$ receptor affinity, and the use of compounds with 5HT$_7$ receptor affinity to lower IOP, improve blood flow to the optic nerve head and the retina, provide neuroprotection, and control damage associated with diseases, such as, glaucoma, ARMD, optic neuritis, ischemic disorders, and retinal edema by functioning as neuroprotectants. Compositions of the compounds are contemplated for such uses. The Compounds are also useful for treating sleep disorders, depression, and other psychiatric disorders, such as, schizophrenia, anxiety, obsessive compulsive disorder, circadian rhythm disorders, and centrally and peripherally mediated hypertension.

DETAILED DESCRIPTION PREFERRED EMBODIMENTS

It has been unexpectedly discovered that 5HT$_7$ receptors are present in the retina, choroid, and possibly the optic nerve head. Furthermore, sertonergic Compounds which possess a relatively high affinity ($K_i$=0.01-200 nM) for 5HT$_7$ receptors effectively lower elevated IOP. It is believed that these Compounds can improve blood flow, and provide neuroprotection to the optic nerve head and the retina. The Compounds' (preferrably Compounds that are agonists or partial agonists) ability to improve blood flow to the optic nerve head and the retina and other characteristics are believed to render them neuroprotective. The novel Compounds disclosed herein are also useful for treating sleep disorders, depression, and other psychiatric disorders.

Compounds found in the following applications are useful according to the present invention and are incorporated herein by reference: EP 738513-A1; WO 97/29097; WO 97/48681; WO 97/49695; and WO 98/00400. Specific Compounds include: LY-215840, SB-258719, and DR-4004.

The following novel Compounds and their pharmaceutically acceptable salts and solvates are useful for treating persons with the diseases and disorders previously described.

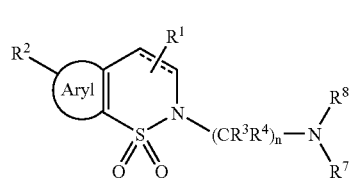

Formula I

Wherein the dashed bond represents a single or double bond;
Aryl signifies a fused phenyl or monocyclic heteroaromatic ring;
R$^1$ is H, OH, OC$_{1-3}$alkyl, C$_{1-3}$alkyl, C$_{1-3}$alkyl substituted optionally with OH, or OC$_{1-3}$alkyl;
R$^2$ is H, halogen, C$_{1-3}$alkyl, CONR$^5$R$^6$, S(=O)$_m$C$_{1-3}$alkyl, S(=O)$_2$NR$^5$R$^6$, C$_{1-3}$alkyl substituted optionally with OH, or OC$_{1-3}$allyl;
R$^3$, R$^4$ are independently H, C$_{1-3}$alkyl, C$_{1-3}$alkyl substituted optionally with OH or OC$_{1-3}$alkyl;
R$^5$, R$^6$ are independently H, C$_{1-3}$alkyl, C$_{2-3}$alkyl substituted optionally with OH, OC$_{1-3}$alkyl, or R$^5$ and R$^6$ can be joined together with saturated carbon atoms to form a 5 or 6 membered ring and said carbon atoms can be either unsubstituted or substituted optionally with C$_{1-3}$alkyl, C$_{2-3}$alkyl substituted optionally with OH or OC$_{1-3}$alkyl;
R$^7$, R$^8$ are together with the nitrogen atom to which they are attached incorporated into a heterocyclic ring of 5 to 8 atoms which may include a second heteroatom selected from N, O, S, such as pyrrolidine, piperidine, Δ$^3$-piperidein, piperazine, morpholine or thiomorpholine which can be unsubstituted or substituted on carbon with one or more substituents optionally selected from C$_{1-3}$alkyl, C$_{1-3}$alkyl substituted optionally with OH, OC$_{1-3}$alkyl, phenyl which can be unsubstituted or substituted optionally with halogen, CF$_3$, OC$_{1-3}$alkyl, or C$_{1-3}$alkyl, or substituted on nitrogen with C$_{1-4}$alkoxy or phenyl which can be unsubstituted or substituted optionally with halogen, CF$_3$, OC$_{1-3}$alkyl, or C$_{1-3}$alkyl;
n is 2 to 4;
m is 0, 1 or 2.

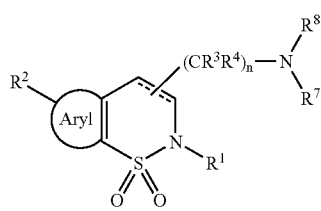

Formula II

Wherein the dashed bond represents a single or double bond;
Aryl signifies a fused phenyl or monocyclic heteroaromatic ring;
R$^1$ is H, C$_{1-5}$alkyl, C$_{3-5}$alkenyl, an aromatic ring such as phenyl, thienyl, pyridyl, and imidazoyl which is either unsubstituted or substituted optionally with OH, OC$_{1-3}$ alkyl, S(=O)$_m$C$_{1-3}$alkyl, halogen, CF$_3$, or S(=O)$_2$NR$^5$R$^6$; or C$_{2-5}$alkyl substituted optionally with OH, OC$_{1-3}$alkyl, S(=O)$_m$C$_{1-3}$alkyl or an aromatic ring such as phenyl, thienyl, pyridyl, and imidazoyl which is either unsubstituted or substituted optionally with OH, OC$_{1-3}$ alkyl, S(=O)$_m$C$_{1-3}$alkyl, halogen, CF$_3$, S(=O)$_2$ NR$^5$R$^6$; or C$_{3-5}$alkenyl substituted optionally with OH, OC$_{1-3}$ alkyl, or S(=O)$_m$C$_{1-3}$alkyl;
R$^2$ is H, halogen, C$_{1-3}$alkyl, S(=O)$_m$C$_{1-3}$alkyl, S(=O)$_2$ NR$^5$R$^6$, or C$_{1-3}$alkyl substituted optionally with OH, or OC$_{1-3}$alkyl;
R$^3$ & R$^4$ are independently H, C$_{1-3}$alkyl, or C$_{1-3}$alkyl substituted optionally with OH or OC$_{1-3}$alkyl;

$R^5$, $R^6$ are independently H, $C_{1-3}$alkyl, $C_{2-3}$alkyl substituted optionally with OH, $OC_{1-3}$alkyl, or $R^5$ and $R^6$ can be joined together with saturated carbon atoms to form a 5 or 6 membered ring and said carbon atoms can be either unsubstituted or substituted optionally with $C_{1-3}$alkyl, $C_{2-3}$alkyl substituted optionally with OH or $OC_{1-3}$alkyl;

$R^7$, $R^8$ are together with the nitrogen atom to which they are attached incorporated into a heterocyclic ring of 5 to 8 atoms which may include a second heteroatom selected from N, O, S, such as pyrrolidine, piperidine, $\Delta^3$-piperidein, piperazine, morpholine or thiomorpholine which can be unsubstituted or substituted on carbon with one or more substituents optionally selected from $C_{1-3}$alkyl, $C_{1-3}$alkyl substituted optionally with OH, $OC_{1-3}$alkyl, phenyl which can be unsubstituted or substituted optionally with halogen, $CF_3$, $OC_{1-3}$alkyl, or $C_{1-3}$alkyl, or substituted on nitrogen with $C_{1-4}$alkoxy or phenyl which can be unsubstituted or substituted optionally with halogen, $CF_3$, $OC_{1-3}$alkyl, or $C_{1-3}$alkyl;

n is 2 to 4;

m is 0, 1 or 2.

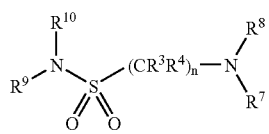

Formula III $R^3$ & $R^4$ are independently H, $C_{1-3}$alkyl, or $C_{1-3}$alkyl substituted optionally with OH or $OC_{1-3}$alkyl;

$R^7$, $R^8$ are together with the nitrogen atom to which they are attached incorporated into a heterocyclic ring of 5 to 8 atoms which may include a second heteroatom selected from N, O, S, such as pyrrolidine, piperidine, $\Delta^3$-piperidein, piperazine, morpholine or thiomorpholine which can be unsubstituted or substituted on carbon with one or more substituents optionally selected from $C_{1-3}$alkyl, $C_{1-3}$alkyl substituted optionally with OH, $OC_{1-3}$alkyl, phenyl which can be unsubstituted or substituted optionally with halogen, $CF_3$, $OC_{1-3}$alkyl, or $C_{1-3}$alkyl, or substituted on nitrogen with $C_{1-4}$alkoxy or phenyl which can be unsubstituted or substituted optionally with halogen, $CF_3$, $OC_{1-3}$alkyl, or $C_{1-3}$alkyl;

$R^9$ is phenyl or a monocyclic heteroaromatic ring which can be unsubstituted or substituted with $C_{1-4}$ alkyl, halogen, $OC_{1-4}$alkyl;

$R^{10}$ is $C_{1-4}$alkyl, or $R^{10}$ can be joined to $R^9$ to form a fused bicyclic ring system such as indoline;

n is 2 to 4.

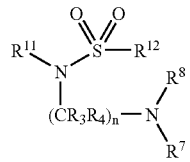

Formula IV $R^3$ & $R^4$ are independently H, $C_{1-3}$alkyl, or $C_{1-3}$alkyl substituted optionally with OH or $OC_{1-3}$alkyl;

$R^7$, $R^8$ are together with the nitrogen atom to which they are attached incorporated into a heterocyclic ring of 5 to 8 atoms which may include a second heteroatom selected from N, O, S, such as pyrrolidine, piperidine, $\Delta^3$-piperidein, piperazine, morpholine or thiomorpholine which can be unsubstituted or substituted on carbon with one or more substituents optionally selected from $C_{1-3}$alkyl, $C_{1-3}$alkyl substituted optionally with OH, $OC_{1-3}$alkyl, phenyl which can be unsubstituted or substituted optionally with halogen, $CF_3$, $OC_{1-3}$alkyl, or $C_{1-3}$alkyl, or substituted on nitrogen with $C_{1-4}$alkoxy or phenyl which can be unsubstituted or substituted optionally with halogen, $CF_3$, $OC_{1-3}$alkyl, or $C_{1-3}$alkyl;

$R^{11}$ is $C_{1-3}$alkyl, phenyl or a monocyclic heteroaromatic ring which can be unsubstituted or substituted with $C_{1-4}$ alkyl, halogen, $OC_{1-4}$alkyl;

$R^{12}$ is $C_{1-4}$alkyl or a fused bicyclic heteroaromatic ring such as thieno[3,2-e]-1,2-thiazine, or 1,2-benzothiazine, or $R^{12}$ can be joined to $R^{11}$ to form a fused bicyclic ring system such as 2,3-dihydro-benzo[c]isoxazole;

n is 2 to 4.

The compounds of the present invention can be prepared using chemical synthesis procedures herein described. The preferred method for preparing compounds of Formula I is illustrated in Scheme I. For example, the thiazine alcohols 1, which can be prepared by methods described in U.S. Pat. Nos. 5,344,929 and 5,470,973, or in *J. Org. Chem.* 31, 162 (1966), can be selectively alkylated on the nitrogen atom at position two with, for example, a dihaloalkane using procedures known to the art to give 2, where X is a halogen atom such as chlorine, bromine, or iodine. Compounds 2 can be treated with amines by known procedures to provide compounds of Formula I (3) where $R^1$ is hydroxyl, further these alcohols 3 can be treated with an alkylhalide to effect alkylation on oxygen to provide the ethers, $R^1$ is alkoxy. Alternately, 2 can be dehydrated by using methods described in U.S. Pat. No. 5,538,966 to give compounds 4 which can be further reacted with amines to give compounds of Formula I where $R^1$ is hydrogen and the thiazine ring contains a double bond (5).

Scheme I

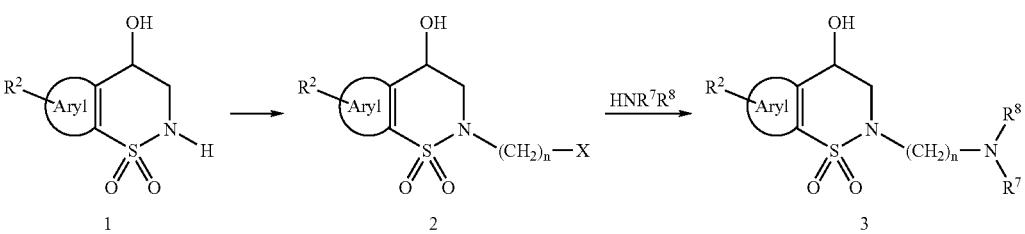

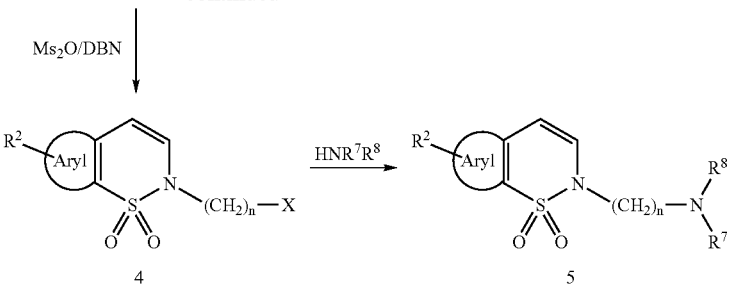

Procedures for preparing compounds of Formula II are illustrated in Scheme II. For example, the 3-hydroxymethyl thiazine compounds 7 can be prepared from the esters 6 by methods described in U.S. Pat. No. 5,538,966 [Equation (a)]. Further, compounds 7 can be aminated using a variety of well known procedures, such as initial activation of the hydroxyl group by forming a sulfonate ester, followed by reaction of this intermediate with the desired primary or secondary amine to give compounds 8 of Formula II where $R^3$ and $R^4$ are hydrogen and n is 1 [Equation (b)]. Additionally, using 7 as an intermediate with which to initiate a suitable homologation sequence, compounds of Formula II wherein $R^3$ and $R^4$ are hydrogen and n is 2 or 3 can be prepared; an example of such a homologation sequence employing 7 is illustrated in Equations (c) and (d), respectively.

Scheme II

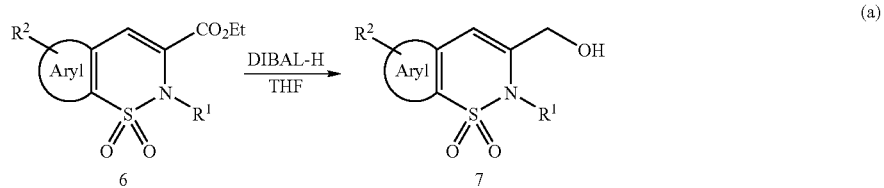

(a)

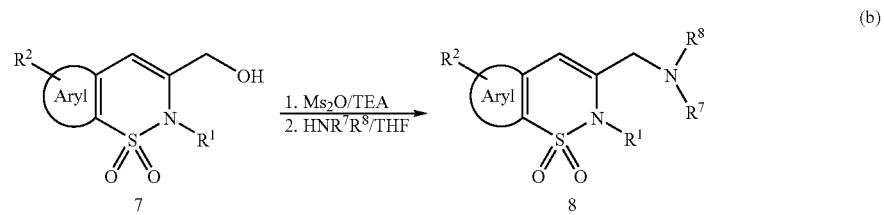

(b)

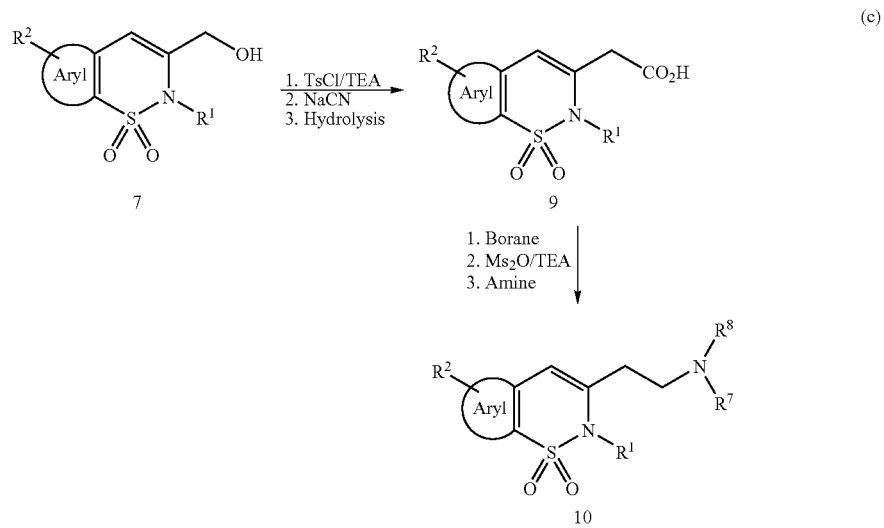

(c)

-continued

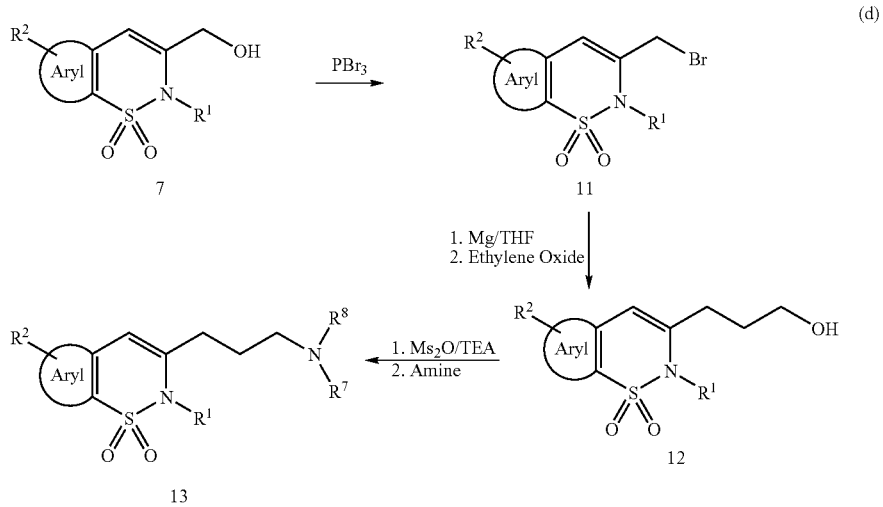

(d)

The preparation of compounds of Formula III can be readily accomplished by procedures herein described. For example, reaction of the desired amine 14 with the appropriate haloalkylsulfonyl chloride 15 in an inert solvent in the presence of a suitable base [see e.g., *J. Med. Chem.* 40, 3217 (1997)] to give the haloalkylsulfonamide intermediate 16. Subsequent reaction of 16 with the appropriate primary or secondary amine employing known procedures, provides compounds 17 of Formula III.

Scheme III

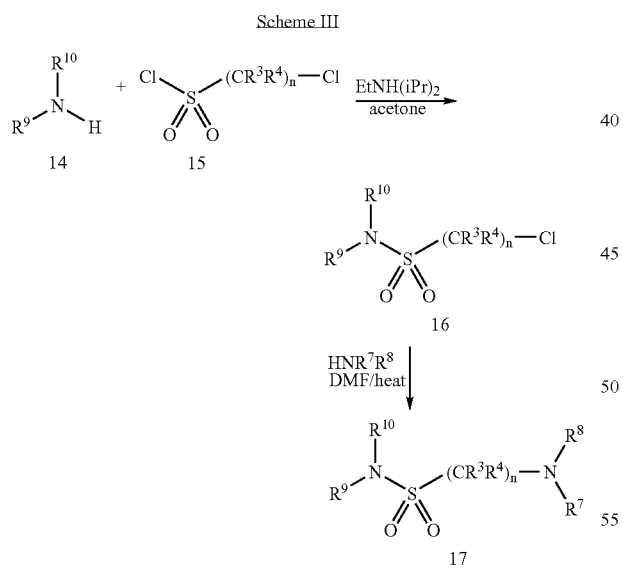

The preparation of compounds of Formula IV can be readily accomplished by procedures herein described. For example, reaction of the desired primary amine 18 with the appropriate sulfonyl chloride in an inert solvent in the presence of a suitable base provides the intermediate secondary sulfonamide 19 which can be alkylated by known procedures with the appropriately substituted alkyldibromide to give the haloalkylsulfonamide intermediate 20. Subsequent reaction of 20 with the appropriate primary or secondary amine employing well known procedures provides compounds 21 of Formula IV.

Scheme IV

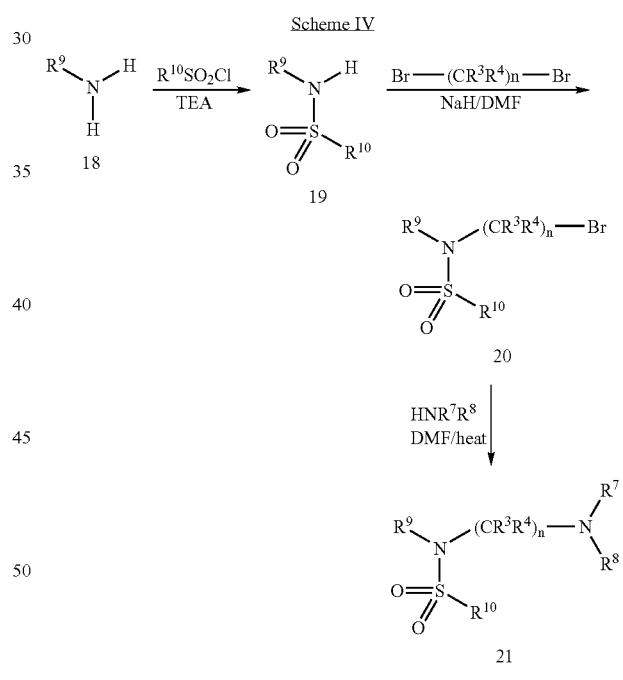

It is evident that some of the Compounds of Formula I-IV will include asymmetric atoms, all enantiomers and diastereomers are contemplated.

The term heteroaromatic ring refers to thiophene, furan, pyrrole, pyridine, pyrimidine, pyridazine and pyrazine.

The Compounds can be administered systemically or locally to the eye (e.g., topically, intracamerally, or via an implant). The Compounds are preferably incorporated into topical ophthalmic formulations for delivery to the eye. The Compounds may be combined with ophthalmologically acceptable preservatives, surfactants, viscosity enhancers, penetration enhancers, buffers, sodium chloride, and water to form an aqueous, sterile ophthalmic suspension or solution. Ophthalmic solution formulations may be prepared by dissolving a Compound in a physiologically acceptable isotonic aqueous buffer. Further, the ophthalmic solution may include an ophthalmologically acceptable surfactant to assist in dissolving the Compound. Furthermore, the ophthalmic solution may contain an agent to increase viscosity, such as, hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-940, or the like, according to the published formulations for analogous ophthalmic preparations; preservatives and tonicity agents can be incorporated. The Compounds can be formulated for systemic (e.g. oral, I.V., I.M., subcutaneous) delivery according to methods known to one skilled in the art. For systemic delivery the Compounds are delivered at concentrations of 0.005-1000 mg. per dose, preferably 0.05-20.0, most preferably 0.2-5 mg. per dose. The Compounds will be dosed 1-4 times per day according to the discretion of a skilled clinician.

For ophthalmic medications the Compounds are preferably formulated as topical ophthalmic suspensions or solutions, with a pH of about 5 to 8. The Compounds will normally be contained in these formulations in an amount 0.01% to 5% by weight, but preferably in an amount of 0.25% to 2% by weight. Thus, for topical presentation 1 to 2 drops of these formulations would be delivered to the surface of the eye 1 to 4 times per day according to the routine discretion of a skilled clinician. The preferred Compounds are those set forth in Examples 1, 1.1, 1.2, 1.6, 1.8, 2.3, 2.7, 2.10, 2.1, 2.4, 3, 3.1, 3.11, 3.5, and 3.10.

EXAMPLE 1

6-Chloro-2-[4-[4-(2H-benzimidazo-2-oxo-1-yl)piperidin-1-yl]butyl]-2H-thieno[3,2-e]-1,2-thiazine 1,1-dioxide Hydrochloride

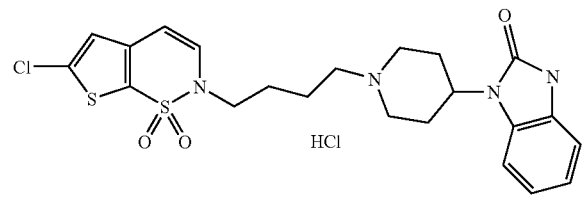

Step 1. A solution 6-chloro-3,4-dihydro-2H-thieno[3,2-e]-1,2-thiazine-4-ol 1,1-dioxide (9.0 g, 37.6 mmol) in dimethylformamide (200 mL, anhydrous) and sodium hydride (60% in oil, 1.66 g, 41.5 mmol) was reacted with 1,4-dibromobutane at 0°. The reaction was stirred in an ice bath for 30 min and then it was allowed to warm to room temperature and stir for three days. The mixture was poured into ice water (400 mL) and extracted with diethyl ether (2×200 mL). The combined organic layers were washed with water (200 mL), brine (200 mL) and then were dried over magnesium sulfate and evaporated. The resulting residue was purified by silica gel flash chromatography with hexane/ethyl acetate (7:3) to give 6-chloro-3,4-dihydro-2-(4-bromobutyl)-2H-thieno[3,2-e]-1,2-thiazine-4-ol 1,1-dioxide as a colorless oil (10.62 g, 75%); the $^1$H NMR was consistent with the structure.

Step 2. The product from Step 1 (10.6 g, 28.3 mmol) was dissolved in tetrahydrofuran (anhydrous, 400 mL) and treated with triethyl amine (9.88 mL, 70.9 mmol) and methane sulfonic anhydride (9.86 g, 56.6 mmol) at room temperature and stirred for one hour. The suspension was concentrated and taken up in dimethylformamide (anhydrous, 120 mL). This mixture was heated at 160° for 45 min. The reaction mixture was poured into ice water (300 ml) and extracted with dichloromethane (300 mL). The organic layer was washed with water (2×200 mL), dried over magnesium sulfate and evaporated to a brown oil. After silica flash chromatography with hexane/ethyl acetate 6-chloro-2-(4-bromobutyl)-2H-thieno[3,2-e]-1,2-thiazine 1,1-dioxide was obtained as a yellow oil (4.97 g, 49%); the $^1$H NMR. was consistent with the structure.

Step 3. A solution of 4-(2H-benzimidazo-2-oxo-1-yl)piperidine (0.30 mmol) in DMF (1.6 mL, anhydrous) and triethyl amine (0.5 mL) was treated with the product of Step 2 (0.103 g, 0.29 mmol) and stirred at 70° for 20 hours and then at room temperature for two days. The reaction mixture was diluted with ethyl acetate (3 mL) and water (4 mL). Saturated sodium bicarbonate (1 mL) was added and the layers were mixed followed by removal of the aqueous layer. The organic layer was washed with water (6 mL) and evaporated to give a residue that was dissolved in ethanol and treated with 1 N hydrochloric acid in ether. After evaporation the desired product was obtained as a white solid (69.2 mg, 45%): $^1$H NMR and MS (M+H 493) were consistent with the structure.

By following the procedures of Example 1, but replacing 4-(2H-benzimidazo-2-oxo-1-yl)piperidine in Step 3 with the appropriate amine, the following compounds were prepared. The $^1$H NMR spectrum and the mass spectrum for each of these compounds were consistent with the assigned structure.

1. 6-Chloro-2-[4-(4-phenylpiperazin-1-yl)butyl]-2H-thieno[3,2-e]-1,2-thiazine 1,1-dioxide hydrochloride;
2. 6-Chloro-2-[4-[4-(2-fluorophenyl)piperazin-1-yl]butyl]-2H-thieno[3,2-e]-1,2-thiazane 1,1-dioxide hydrochloride;
3. 6-Chloro-2-[4-[4-hydroxy-4-(4-chlorophenyl)piperidin-1-yl]butyl]-2H-thieno[3,2-e]-1,2-thiazine 1,1-dioxide hydrochloride;
4. 6-Chloro-2-[4-[4-hydroxypiperidin-1-yl]butyl]-2H-thieno[3,2-e]-1,2-thiazine 1,1-dioxide hydrochloride.

By following the procedures of Example 1, but replacing the 1,4-dibromobutane in Step 1 with 1,3-dibromopentane and 4-(2H-benzimidazo-2-oxo-1-yl)piperidine in Step 3 with the appropriate amine, the following compounds were prepared. The $^1$H NMR spectrum and the mass spectrum for each of these compounds were consistent with the assigned structure.

5. 6-Chloro-2-[3-[4-phenylpiperazin-1-yl]propyl]-2H-thieno[3,2-e]-1,2-thiazine 1,1-dioxide hydrochloride;
6. 6-Chloro-2-[3-[4-(3-trifluoromethylphenyl)piperazin-1-yl]propyl]-2H-thieno[3,2-e]-1,2-thiazine 1,1-dioxide hydrochloride;
7. 6-Chloro-2-[3-[4-(2-fluorophenyl)piperazin-1-yl]propyl]-2H-thieno[3,2-e]-1,2-thiazine 1,1-dioxide hydrochloride;
8. 6-Chloro-2-[3-[4-(2H-benzimidazol-2-oxo)piperidin-1-yl]propyl]-2H-thieno[3,2-e]-1,2-thiazine 1,1-dioxide hydrochloride.

EXAMPLE 2

3-(4-Methylpiperidin-1-yl)propylsulfonyl-2,3-dihydro-1H-indole Hydrochloride

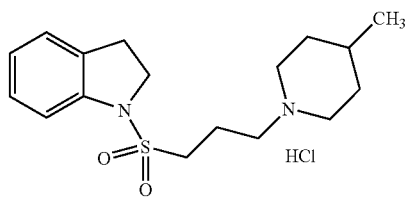

Step 1. To a solution of indoline (4.00 g, 33.6 mmol) in 100 mL of acetone at 0° C. was added 3-chloropropanesulfonyl chloride (5.95 g, 33.6 mmol) with stirring. A solid precipitated from the solution. Diisopropylethylamine (4.33 g, 33.6 mmol) was added in two portions and the reaction mixture became a homogenous solution. The mixture was stirred for 30 min, warmed to ambient temperature, and evaporated to dryness. The crude mixture was combined with a saturated aqueous solution of sodium bicarbonate and extracted with ethyl acetate (2×100 mL). Chromatography on silica (10% to 25% ethyl acetate/hexane) gave an oil which solidified on standing (7.68 g, 77%, mp 53-53° C.).

Step 2. A mixture of the product of Step 1 (200 mg, 0.77 mmol) and 0.5 M solution of 4-methylpiperidine (4 mL, 2.0 mmol) was heated at 35° C. for 60 h. The reaction mixture was combined with a saturated aqueous solution of sodium bicarbonate and extracted with ethyl acetate (2×10 mL). The extracts were dried and evaporated to dryness. The crude product was filtered though a short silica column and treated with a 1.0 M solution of hydrogen chloride gas in ether. The solid was filtered and dried to give the hydrochloride salt (220 mg, 80%): MS(ES) 323 (M+H).

By following the procedures of Example 2, but replacing 4-methylpiperidine in Step 2 with the appropriate amine, the following compounds were prepared. The $^1$H NMR spectrum and the mass spectrum for each of these compounds were consistent with the assigned structure.

1. 3-[4-(3-Chlorophenyl)piperazin-1-yl]propylsulfonyl-2,3-dihydro-1H-indole;
2. 3-(3-Methylpiperidin-1-yl)propylsulfonyl-2,3-dihydro-1H-indole;
3. 3-(1,2,3,4-Tetrahydroisoquinolin-2-yl)propylsulfonyl-2,3-dihydro-1H-indole;
4. 3-[4-(3-Trifluoromethylphenyl)piperazin-1-yl]propylsulfonyl-2,3-dihydro-1H-indole;
5. 3-(4-Phenylpiperazin-1-yl)propylsulfonyl-2,3-dihydro-1H-indole;
6. 3-[4-(2-Fluorophenyl)piperazin-1-yl]propylsulfonyl-2,3-dihydro-1H-indole;
7. 3-[4-(2-Methoxyphenyl)piperazin-1-yl]propylsulfonyl-2,3-dihydro-1H-indole;
8. 3-[4-(4-Methoxyphenyl)piperazin-1-yl]propylsulfonyl-2,3-dihydro-1H-indole;
9. 3-[4-(2-Chlorophenyl)piperazin-1-yl]propylsulfonyl-2,3-dihydro-1H-indole.

By following the procedures of Example 2, but replacing the indoline in Step 1 with N-methylaniline and the 4-methylpiperidine in Step 2 with the appropriate amine, the following compounds were prepared. The $^1$H NMR spectrum and the mass spectrum for each of these compounds were consistent with the assigned structure.

10. 3-(1,2,3,4-Tetrahydroisoquinolin-2-yl)-N-methyl-N-phenyl-propylsulfonamide;
11. N-Methyl-N-phenyl-3-[4-(3-trifluoromethylphenyl)piperazin-1-yl]propylsulfonamide;
12. N-Methyl-N-phenyl-3-(4-phenylpiperazin-1-yl)propylsulfonamide;
13. 3-[4-(2-Fluorophenyl)piperazin-1-yl]-N-methyl-N-phenyl-propylsulfonamide;
14. N-Methyl-3-[4-(2-methoxyphenyl)piperazin-1-yl]-N-phenyl-propylsulfonamide;
15. 3-[4-(2-Chlorophenyl)piperazin-1-yl]-N-methyl-N-phenyl-propylsulfonamide By following the procedures of Example 2, but replacing the 3-chloropropanesulfonyl chloride in Step 1 with 2-chloroethanesulfonyl chloride and the 4-methylpiperidine in Step 2 with 3-methylpiperidine, the following compound was prepared. The $^1$H NMR spectrum and the mass spectrum for this compound were consistent with the assigned structure.

16. 2-(3-Methylpiperidin-1-yl)ethylsulfonyl-2,3-dihydro-1H-indole.

EXAMPLE 3

N-[3-[4-(3-Chlorophenyl)piperazin-1-yl]propyl]-N-(4-methoxyphenyl)-propanesulfonamide Hydrochloride

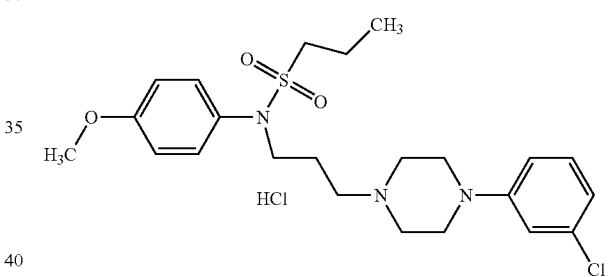

Step 1. To a solution of p-anisidine (6.00 g, 48.7 mmol) and triethylamine (5.91 g, 58.4 mmol) in methylene chloride (200 mL) at 0° C. was added propylsulfonyl chloride (7.64 g, 53.6 mmol) with stirring under nitrogen atmosphere. The reaction mixture was allowed to warm to room temperature and stirred overnight. The mixture was washed with a saturated aqueous solution of sodium bicarbonate (100 mL), water, and dried over magnesium sulfate. The organic layer was evaporated to give an oil that was mixed with a solution of hexane and ethyl acetate (3:1) to afford a crystalline solid (7.97 g). The mother liquid was chromatographed on silica (hexane/ethyl acetate, 4:1) to give a solid (2.27 g, 92%): mp 72° C.; MS(−ES) 228 (M−H).

Step 2. To the product of Step 1 (3.50 g, 15.3 mmol) in anhydrous dimethylformamide (80 mL) at 0° C. was added sodium hydride (60% suspension in mineral oil, 0.672 g, 16.8 mmol) under a nitrogen atmosphere. The suspension was stirred for 30 min and 1,3-dibromopropane (9.27 g, 45.9 mmol) was added over 1 min. The reaction was stirred for 3 h, mixed with a saturated aqueous solution of sodium bicarbonate (200 mL) and extracted with ethyl acetate (3×100 mL). The combined extracts were dried and evaporated to dryness. Chromatography on silica (20% ethyl acetate in hexane) gave a colorless oil (4.33 g, 81%): MS(+ES) 352 (M+H).

Step 3. To a solution of the product of Step 2 (0.175 g, 0.50 mmol) in anhydrous dimethylformamide (1 mL) was added a 0.5 M solution of 1-(3-chlorophenyl)piperazine in dimethylformamide (1.1 mL, 0.55 mmol) and triethylamine (0.20 mL); this mixture was heated at 60° C. for 18 h. The cooled reaction mixture was extracted with ethyl acetate (2×1 mL) and the combined extracts were washed with a saturated aqueous solution of sodium bicarbonate, dried and evaporated to an oil which was treated with a 1.0 M solution of hydrogen chloride gas in ether to give the corresponding salt (0.11 g, 44%): MS(ES) 466 (M+).

By following the procedures of Example 3, but replacing 1-(3-chlorophenyl)piperazine in Step 3 with the appropriate amine, the following compounds were prepared. The $^1$H NMR spectrum and the mass spectrum for each of these compounds were consistent with the assigned structure.

1. N-[3-(1,2,3,4-Tetrahydroisoquinolin-2-yl)propyl]-N-(4-methoxyphenyl)-propanesulfonamide;
2. N-[3-(3-Hydroxymethylpiperidin-1-yl)propyl]-N-(4-methoxyphenyl)-propanesulfonamide;
3. N-(4-Methoxyphenyl)-N-[3-(morpholin-4-yl)propyl]-propanesulfonamide;
4. N-(4-Methoxyphenyl)-N-[3-(2-methylpiperidin-1-yl)propyl]-propanesulfonamide;
5. N-[3-[4-(3-Chlorophenyl)piperazin-1-yl]propyl]-N-(4-methoxyphenyl)-propanesulfonamide;
6. N-(4-Methoxyphenyl)-N-[3-[4-(3-trifluoromethylphenyl)piperazin-1-yl]propyl]-propanesulfonamide;
7. N-[3-(4-phenylpiperazin-1-yl)propyl]-N-(4-methoxyphenyl)-propanesulfonamide;
8. N-[3-[4-(2-Fluorophenyl)piperazin-1-yl]propyl]-N-(4-methoxyphenyl)-propanesulfonamide;
9. N-[3-[4-(4-Methoxyphenyl)piperazin-1-yl]propyl]-N-(4-methoxyphenyl)-propanesulfonamide;
10. N-[3-[4-(2-Methoxyphenyl)piperazin-1-yl]propyl]-N-(4-methoxyphenyl)-propanesulfonamide;
11. N-[3-[4-(2-Chlorophenyl)piperazin-1-yl]propyl]-N-(4-methoxyphenyl)-propanesulfonamide;
12. N-[3-[4-(2H-Benzimidazo-2-oxo-1-yl)piperidin-1-yl]propyl]-N-(4-methoxyphenyl)-propanesulfonamide.

By following the procedures of Example 3, but replacing the 1,3-dibromopropane in Step 2 with 1,4-dibromobutane and the 1-(3-chlorophenyl)piperazine in Step 3 with 1,2,3,4-tetrahydroisoquinoline, the following compound was prepared. The $^1$H NMR spectrum and the mass spectrum for this compound were consistent with the assigned structure.

13. N-[4-(1,2,3,4-Tetrahydroisoquinolin-2-yl)butyl]-N-(4-methoxyphenyl)-methanesulfonamide.

The following topical ophthalmic formulations are useful according to the present invention administered 1-4 times per day according to the discretion of a skilled clinician.

EXAMPLE 4

| Ingredients | Amount (wt %) |
| --- | --- |
| 5HT$_7$ Compound | 0.01-2% |
| Hydroxypropyl methylcellulose | 0.5% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

EXAMPLE 5

| Ingredients | Amount (wt %) |
| --- | --- |
| 5HT$_7$ Compound | 0.01-2% |
| Hydroxypropyl methylcellulose | 0.5% |
| Cremophor EL | 0.1% |
| Tromethamine, USP, AR | 0.64% |
| Mannitol, USP | 3.0% |
| Boric acid, USP | 0.3% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

EXAMPLE 6

| Ingredients | Amount (wt %) |
| --- | --- |
| 5HT$_7$ Compound | 0.01-2% |
| Methyl cellulose | 4.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

EXAMPLE 7

| Ingredients | Amount (wt %) |
| --- | --- |
| 5HT$_7$ Compound | 0.01-2% |
| Hydroxypropyl-β-cyclodextrin | 4.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

EXAMPLE 8

| Ingredients | Amount (wt %) |
|---|---|
| 5HT$_7$ Compound | 0.01-2% |
| Xanthan gum | 0.5-6.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

EXAMPLE 9

| Ingredients | Amount (wt %) |
|---|---|
| 5HT$_7$ Compound | 0.01-2% |
| Guar gum | 0.4-6.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

EXAMPLE 10

| Ingredients | Amount (wt %) |
|---|---|
| 5HT$_7$ Compound | 0.01-2% |
| Tyloxapol | 0.2-4.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

EXAMPLE 11

| Ingredients | Amount (wt %) |
|---|---|
| 5HT$_7$ Compound | 0.01-2% |
| White petrolatum and mineral oil and lanolin | Ointment consistency |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |

EXAMPLE 12

Formulation for Oral Administration

Tablet: 0.2-5 mg. of 5HT$_7$ Compound with inactive ingredients such as cornstarch, lactose, colloidal silicon dioxide, microcrystalline cellulose, and magnesium sterate can be formulated according to procedures known to those skilled in the art of tablet formulation.

We claim:

1. A compound of the formula:

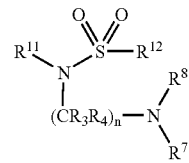

$R^3$, $R^4$ are independently H, $C_{1-3}$alkyl, or $C_{1-3}$alkyl substituted optionally with OH or $OC_{1-3}$alkyl;

$R^7$, $R^8$ are together with the nitrogen atom to which they are attached form a heterocyclic ring selected from the group consisting of piperazine, which is substituted on carbon with one or more substituents optionally selected from $C_{1-3}$alkyl, $C_{1-3}$alkyl substituted optionally with OH, $OC_{1-3}$alkyl, phenyl which can be unsubstituted or substituted optionally with halogen, $CF_3$, $OC_{1-3}$alkyl, or $C_{1-3}$alkyl;

$R^{11}$ is phenyl or a monocyclic heteroaromatic ring which can be unsubstituted or substituted with $C_{1-4}$alkyl, halogen, $OC_{1-4}$alkyl;

$R^{12}$ is $C_{1-4}$alkyl or a fused bicyclic heteroaromatic ring selected from the group consisting of thieno[3,2-e]-1,2-thiazine, and 1,2-benzothiazine, or $R^{12}$ can be joined to $R^{11}$ to form 1,3-dihydro-benzo[c]isothiazole;

n is 2 to 4 or a pharmaceutically acceptable salt thereof.

2. A topically administrable ophthalmic composition comprising a pharmaceutically effective amount of a compound of the formula:

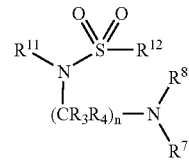

$R^3$, $R^4$ are independently H, $C_{1-3}$alkyl, or $C_{1-3}$alkyl substituted optionally with OH or $OC_{1-3}$alkyl;

$R^7$, $R^8$ are together with the nitrogen atom to which they are attached form a heterocyclic ring selected from the group consisting of piperazine, which is substituted on carbon with one or more substituents optionally selected from $C_{1-3}$alkyl, $C_{1-3}$alkyl substituted optionally with OH, $OC_{1-3}$alkyl, phenyl which can be unsubstituted or substituted optionally with halogen, $CF_3$, $OC_{1-3}$alkyl, or $C_{1-3}$alkyl, $R^{11}$ is phenyl or a monocyclic heteroaromatic ring which can be unsubstituted or substituted with $C_{1-4}$alkyl, halogen, $OC_{1-4}$alkyl;

$R^{12}$ is $C_{1-4}$alkyl or a fused bicyclic heteroaromatic ring selected from the group consisting of thieno[3,2-e]-1,2-thiazine, and 1,2-benzothiazine, or $R^{12}$ can be joined to $R^{11}$ to form 1,3-dihydro-benzo[c]isothiazole;

n is 2 to 4 or a pharmaceutically acceptable salt thereof.

* * * * *